United States Patent
Mallinson

(10) Patent No.: US 11,513,596 B2
(45) Date of Patent: Nov. 29, 2022

(54) EEG WITH ARTIFICIAL INTELLIGENCE AS CONTROL DEVICE

(71) Applicant: SiliconIntervention Inc., Kelowna (CA)

(72) Inventor: A. Martin Mallinson, Kelowna (CA)

(73) Assignee: SiliconIntervention Inc., Kelowna (CA)

( * ) Notice: Subject to any disclaimer, the term of this patent is extended or adjusted under 35 U.S.C. 154(b) by 317 days.

(21) Appl. No.: 16/849,794

(22) Filed: Apr. 15, 2020

(65) Prior Publication Data
US 2020/0333882 A1   Oct. 22, 2020

Related U.S. Application Data
(60) Provisional application No. 62/834,866, filed on Apr. 16, 2019.

(51) Int. Cl.
*G06F 3/01* (2006.01)
*G06N 3/04* (2006.01)
(Continued)

(52) U.S. Cl.
CPC .............. *G06F 3/015* (2013.01); *A61B 5/369* (2021.01); *A61B 5/7246* (2013.01);
(Continued)

(58) Field of Classification Search
CPC ......... G06F 3/015; G06F 3/017; A61B 5/369; A61B 5/7246; A61B 5/7282; A61B 5/7264; G06N 3/0472; G06N 3/049; G06N 3/0445; G06N 3/08; G06N 3/0454; A63F 13/21; A63F 13/212; A63F 13/837
See application file for complete search history.

(56) References Cited

U.S. PATENT DOCUMENTS

| | | | |
|---|---|---|---|
| 10,607,134 B1* | 3/2020 | Cosic | G06N 3/084 |
| 2017/0035313 A1* | 2/2017 | Hong | A61B 5/389 |

(Continued)

OTHER PUBLICATIONS

Nick Lavers, "Thought-controlled drones may be just the first step in aviation revolution," New Atlas Feb. 25, 2015, ("http://tekevernews.blogspot.com.au/2015/02/using-justyour-brain-to-control-drone.html").

(Continued)

*Primary Examiner* — Ryan W Sherwin
(74) *Attorney, Agent, or Firm* — Gard & Kaslow LLP

(57) ABSTRACT

Described herein is a system and method for controlling a computing system by an AI network based upon an electro-encephalograph (EEG) signal from a user. The user's EEG signals are first detected as the user operates an existing controller, during which time the associated artificial intelligence (AI) system learns by correlating the EEG signals with the commands received from the controller. Once the AI system determines that there is sufficient correlation to predict the user's actions, it can take control of the computing system and initiate commands based upon the user's EEG signal in place of the user's actions with the controller. At this point, weights in the AI network may be locked so that further commands from the controller, or the lack thereof, do not reduce correlation with the EEG signals. In some embodiments, the AI network may initiate commands faster than the user would be able to do.

6 Claims, 3 Drawing Sheets

(51) Int. Cl.
  *A61B 5/00*   (2006.01)
  *A61B 5/369*  (2021.01)
(52) U.S. Cl.
  CPC ........... *A61B 5/7282* (2013.01); *G06N 3/049* (2013.01); *G06N 3/0472* (2013.01)

(56) References Cited

U.S. PATENT DOCUMENTS

| | | | |
|---|---|---|---|
| 2018/0020978 A1* | 1/2018 | Kaifosh | G06F 3/011 |
| | | | 702/150 |
| 2019/0073605 A1* | 3/2019 | Keller | A61B 5/316 |
| 2019/0101977 A1* | 4/2019 | Armstrong-Muntner | |
| | | | G06N 20/00 |
| 2020/0286505 A1* | 9/2020 | Osborne | G06F 3/011 |

OTHER PUBLICATIONS

Jane McGrath, "How the Emotiv EPOC Works" Dec. 10, 2008, HowStuffWorks.com, ("https://electronics.howstuffworks.com/emotiv-epoc.htm").

Joana Pereira, Patrick Ofner, Andreas Schwarz, Andreea Ioana Sburlea, and Gernot R. Muller-Putz, "EEG neural correlates of goal-directed movement intention," Neuroimage Apr. 1, 2017; 149; 129-140.

"Supervised learning," Wikipedia, Apr. 5, 2019, ("https://en.wikipedia.org/w/index.php?title=Supervised_learning&oldid=891115450").

"Recurrent neural network," Wikipedia, Mar. 28, 2019, ("https://en.wikipedia.org/w/index.php?title=Recurrent_neural_network&oldid=889817533").

* cited by examiner

EEG WITH ARTIFICIAL INTELLIGENCE AS CONTROL DEVICE

This application claims priority from Provisional Application No. 62/834,866, filed Apr. 16, 2019, which is incorporated by reference herein in its entirety.

FIELD OF THE INVENTION

The present invention relates generally to artificial intelligence (AI) networks, and more particularly to the use of electroencephalograph (EEG) signals by AI networks.

BACKGROUND OF THE INVENTION

Neural Networks (NN) are the basis of Artificial Intelligence (AI) solutions to problems such as handwriting recognition, image recognition and voice analysis. Certain forms of AI, for example voice or speech analysis, require that the AI system have some knowledge of the signal distributed across time. Speech analysis thus requires that the AI system be able to compare the evolution of the audio signal in time against some learned template.

A class of neural networks known in the art, commonly referred to as Recurrent Neural Networks (RNNs), introduce the ability to analyze evolution over time by providing feedback in one or more layers of the neural network. Various types of AI networks are known in the prior art.

An EEG detector can detect an EEG signal representing the brain waves of a person, and can be analyzed to indicate the person's intent. In some instances, an EEG signal has been used to allow a user to control a device, such as a drone or a game, for example, a simple video game.

It is desirable to allow AI networks to control multiple types of computing devices based upon the EEG signals of a user.

SUMMARY OF THE INVENTION

Described herein is a system and method for controlling a computing system by an AI network based upon an electroencephalograph (EEG) signal from a user.

One embodiment describes a method of controlling a computing system that performs actions based upon input from a controller that represents actions of a user, comprising: receiving by an electroencephalograph (EEG) detector an EEG signal representing the brain wave activity of a user; determining by an artificial intelligence (AI) network a likelihood that an action of the user can be predicted based upon the EEG signal; when the likelihood that the action of the user can be predicted exceeds a predetermined threshold, initiating by the AI network an AI network input to the computing system that represents the predicted action of the user; receiving at the computing system and the AI network an input from the controller representing the action of the user; and updating by the AI network weights in the AI network to better correlate the received EEG signal with the input received from the controller.

In a further embodiment of the method, wherein initiating by the AI network the AI network input to the computing system further comprises substituting by the AI network the AI network input for the controller input.

In a still further embodiment of the method, wherein initiating by the AI network the AI network input to the computing system further comprises initiating the AI network input to the computing system before the controller input would be received by the computing system.

In a yet further embodiment of the method, wherein initiating by the AI network the AI network input to the computing system further comprises: determining that initiating the AI input to the computing system before the controller input has degraded the performance of the computing system; and wherein initiating by the AI network the AI network input to the computing system is delayed while still being before the controller input would be received by the computing system.

A further embodiment describes a system for controlling a computing system that performs actions based upon input from a controller that represents actions of a user, comprising: an electroencephalograph (EEG) detector configured to receive an EEG signal representing the brain wave activity of a user; and an artificial intelligence (AI) network configured to: determine a likelihood that an action of the user can be predicted based upon the EEG signal; when the likelihood that the action of the user can be predicted exceeds a predetermined threshold, initiate an AI network input to the computing system that represents the predicted action of the user; and update weights in the AI network to better correlate the received EEG signal with the input received from the controller.

In a further embodiment of the system wherein the AI network is further configured to initiate the AI network input to the computing system by substituting the AI network input for the controller input.

In a still further embodiment of the system wherein the AI network is further configured to initiate the AI network input to the computing system before the controller input would be received by the computing system.

In a yet still further embodiment of the system wherein the AI network is further configured to: determine that initiating the AI network input to the computing system before the controller input has degraded the performance of the computing system; and delay initiating the AI network input to the computing system while still initiating the AI network input before the controller input would be received by the computing system.

DETAILED DESCRIPTION OF THE INVENTION

Described herein is a system and method for controlling a computing system by an AI network based upon an electroencephalograph (EEG) signal from a user. The system and method improves upon the prior art use of EEG for video games, robots and other computing systems by allowing the user's EEG signals to be detected at first as the user operates an existing controller, during which time the associated artificial intelligence (AI) system learns by correlating the EEG signals with the commands received from the controller. Once the AI system determines that there is sufficient correlation to predict the user's actions, the AI system can take control of the computing system and initiate commands based upon the user's EEG signal in place of the user's actions on the controller.

Once the AI network takes control, weights in the AI network may be locked so that further commands from the controller, or the lack thereof, do not reduce correlation with the EEG signals. In some embodiments, the AI network may initiate commands faster than the user would be able to do, unless doing so degrades performance of the computing system.

Consider, for example, a video game running on a computing system. A user often holds a controller in the hand and uses it to direct action in the video game. If an EEG detector is able to detect the user's EEG signals, and an AI network receives both the EEG signals and the commands from the controller, the AI network can correlate the EEG signal with the action being taken at that time by the user and thus "learn" the user's intent based upon the EEG signals.

For example, as the user activates a "shoot" gesture, such as by using a button or trigger on the hand controller, the EEG detector will record the user's EEG signal in the milliseconds leading up to that hand movement. By correlating the EEG signal with the "shoot" command received from the controller, as would be understood by one of skill in the art in light of the teachings herein, the AI network can improve its ability to determine that a given EEG signal indicates the user's intent to "shoot." Eventually, the AI network can apply a threshold, such as 98% accuracy in predicting the "shoot" gesture, and at this point it can begin to issue the gesture command itself.

Once the AI network has made this determination, the user will begin to experience something different, i.e., at a point in the game the user will find, for example, that the gun shoots before he moves his finger on the hand controller. In this situation, the AI network has taken over for that gesture and exploited the fact that the EEG signal that is now associated with the shoot gesture is present before the hand movement by some number of milliseconds.

Figure 1:
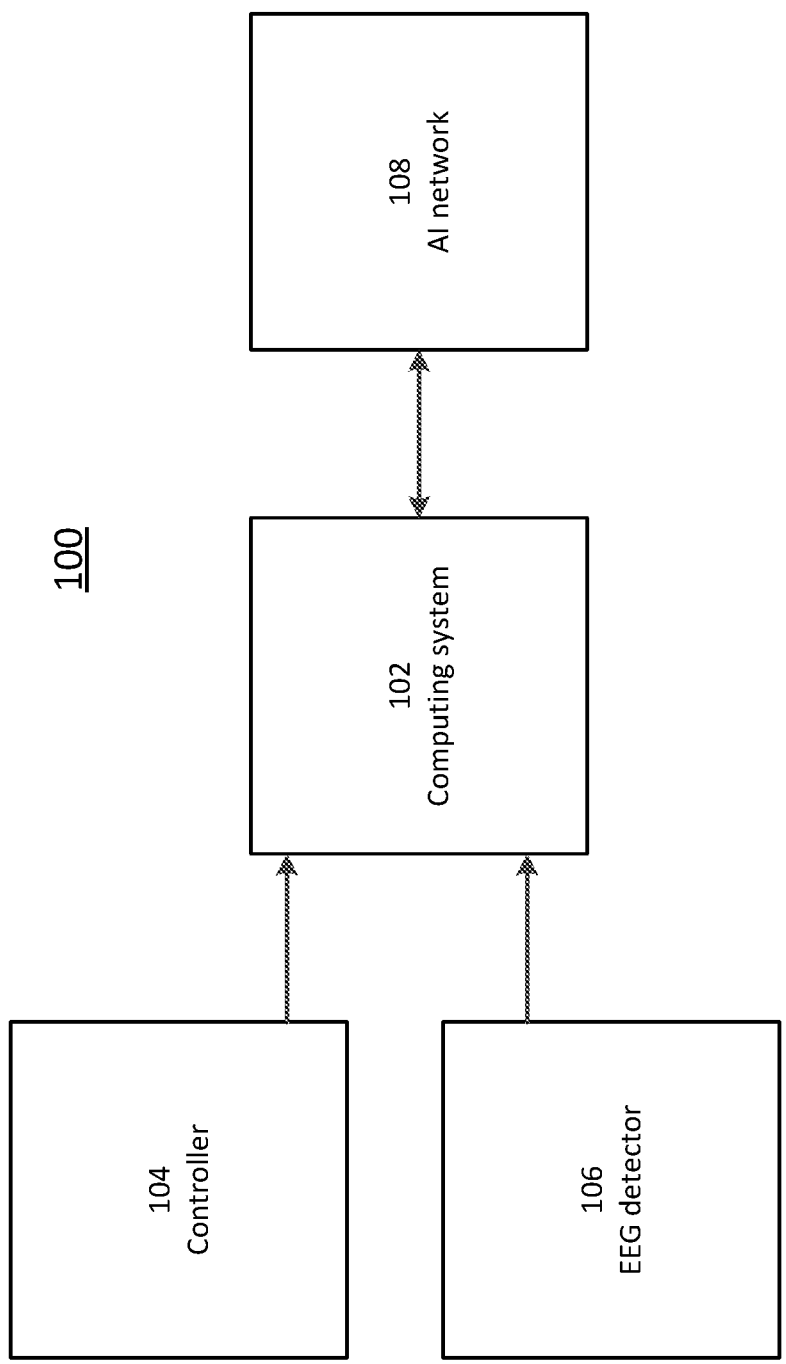
FIG. 1 is a diagram of a system for controlling the actions of a computing system based upon the EEG of a user according to one embodiment.

A system as described herein will generally contain several elements as seen in FIG. 1. FIG. 1 is a diagram of a system 100 for controlling the actions of a computing system based upon the EEG of a user according to one embodiment. As illustrated here, system 100 contains a computing system 102, a controller 104, an EEG detector 106 and an AI network 108.

Computing system 102 receives commands from controller 104 and may be, for example, a game, a robot operating in a warehouse or some similar system which runs on a processor and receives commands based upon some body movement, activity or controlling gesture of a user. Controller 104, for example a game controller, computing system mouse, or other known type of controller, contains a means, for example a button, trigger, touch sensor, etc., to receive input such as body movement, activity, or controlling gestures from the user, such as finger pressure, trigger pulls, hand gestures and so forth; and a means to issue commands to the computing system based upon such input.

One common type of controller is that which is used for a video game, which may, for example, contain one or more buttons that can be pushed, one or more triggers that can be pulled, one or more pressure or capacitive touch sensors, and joysticks or directional arrows that can be activated to perform certain actions in the game.

EEG detector 106 is capable of sensing the user's EEG, i.e., "brain wave" signals; it is expected that such a detector will be located on the user's head in a helmet, headset or some similar device. AI network 108 may be, for example, an RNN, such as an Elman or Jordan network, LSTM network or similar, that includes the means to learn when presented with training data, and will receive both the EEG signals from EEG detector 106 and the commands from the controller 104. In some embodiments, AI network 108 may be located within computing system 102.

The components of system 100 are configured to operate in two distinct phases, or modes. First, system 100 operates in a "learning phase" in which AI network 108 is learning which EEG signals correspond to which user actions. Once AI network 108 has learned which EEG signals correspond to which user actions, system 100 operates in a "controlling phase" in which the AI system is issuing or initiating controller actions.

AI network 108 may be programmed to include a threshold such that when the prediction of the controller action by the AI network using the EEG detector input exceeds the threshold, the AI network begins to send predicted gesture action to the computer system, i.e., it controls the computer system autonomously.

The learning phase of an AI network such as AI network 108 is well known in the art, and has been used, for example, for voice recognition or handwriting recognition. In this phase, an AI network operates in what is known as a "supervised learning mode" and receives "labeled training data," i.e., data which the AI network uses to establish correlations to another input, from which weights in the AI network are determined.

The labeled training data in the video game example herein consists of the flow of information from the controller. The other input corresponding to this labeled training data is the recent input from the EEG detector, here EEG detector 106. Each instance of labeled training data is an instance of the possible controller gestures, commands or inputs. For example, within a game or while controlling a robot there are a finite number of possible gestures, e.g., lift the right arm, rotate the left wrist, shoot the gun, pick up the prize, duck, run, etc. Consequently, AI network 108 is being trained to categorize the input from EEG detector 106 as one of these possible gestures.

The EEG signal that is most closely correlated to an instance of labeled training data is that recorded most recently, that is, a short time ago. This implies that AI network 108 has some time domain aspect, such as Long short-term Memory (LSTM), or is of the Recurrent Neural Network (RNN) type allowing it to access the recent state of the input from the EEG detector.

AI network 108 learns to categorize the signal from EEG detector 106 by employing any of the methods known in the art, such as the Gradient Decent or Global methods. Over time, as the user continues to use controller 104 in the usual way, e.g., playing the game normally, the user is providing more and more training data to AI network 108.

Eventually, AI network 108 will begin to categorize or correlate the gestures correctly; in some embodiments, this degree of "correctness" will be made evident by the relative probability of other gestures. For example, an output value from AI network 108 is assessed for each possible gesture, such as a number between 0 and 1 for each gesture. Initially, the value of these numbers will be similar: a signal from EEG detector 106 will be propagated approximately equally to all gestures when AI network 108 does not yet "know" what gesture this EEG signal represents. Consequently, all output values will initially have a similar number between 0 and 1 present in them.

The command from controller 104 represents the actual gesture that was initiated by user that corresponds to the recent EEG signal. This means the learning algorithm may adjust the weights in AI network 108 to favor the particular value corresponding to this gesture. Incremental changes to the weights may be made to suppress all the gestures that are not the one indicated by the command from controller 104.

As the number of commands from controller 104 increases, the learning algorithm will be able to refine the predicted gesture. In a simplistic example, an EEG signal might have a correlated value for the gesture to "shoot a gun" in the game of 0.9 associated with it while all the other gestures have an associated value of 0.2 or lower. This may indicate that AI network 108 can now make a good prediction of the shoot gesture based upon that particular EEG signal.

In practice, however, the process may be more complicated than that. In this example, if an EEG signal has a correlated value with the shoot gesture of 0.9, while other gestures correlate at lower values, it may be more useful to look at how far the value for one gesture exceeds the values for the others, rather than merely looking at the absolute values for each gesture. Thus, in one embodiment, for example, the reliability of the gesture prediction may be calculated as the ratio of the expected gesture value to the root mean square (RMS) sum of the unexpected gestures.

In the known art an AI network may be continuously learning, for example, continually improving the accuracy with which it can identify an object or person in a picture. However, in these cases the AI network is not predicting what action a user wishes to take. The system and method described herein goes beyond the known art by switching operation from such a passive accumulation of data in a learning mode to an active substitution of the user's action by an action of the AI network.

Thus, for example, when the reliability of the prediction of a specific gesture of the user exceeds a certain threshold, the particular gesture is ready to move into the controlling phase. That is, for such a gesture AI network 108 can now initiate a signal to computing system 102 in place of the signal that is expected from controller 104.

It is not necessary to switch all gestures to the controlling phase simultaneously; rather, only those gestures that meet a certain threshold may enter the controlling phase. This reflects the fact that reaching a certain threshold of "confidence" in predicting a gesture takes time. The occurrence of, for example, a "shoot gun" gesture may be more frequent than a "pick up a prize" gesture, and this will result in the AI network being able to predict a gun shot before it is able to predict the prize pickup.

It will be apparent to one of skill in the art that, in order to switch a gesture to the controlling phase, the weights of the entire AI network that controls that gesture may no longer be changing but rather must be fixed. Thus, in one embodiment, to switch only one of multiple gestures to the controlling phase, the gesture to be separately switched must be controlled by a separate AI network from the other gestures.

In some embodiments there will be a single AI network 180 with multiple layers, each gesture being represented by a neuron value in the final or output layer in the AI network. In such cases, all of the gestures must be ready to switch to the controlling phase before any of the gestures can be switched. This is because until all of the gestures can be predicted to the desired level of accuracy, the weights in the AI network are still changing as the AI network is still learning from the controller command and EEG inputs.

In some embodiments, it may be beneficial to provide some form of feedback to the user, for example, a visual bar graph, of the progress of the categories to this controlling phase. This will allow the user to modify his or her actions to "push a gesture into the controlling phase" by generating additional instances of the gesture. For example, seeing that the "jump left" gesture is nearing the confidence level at which the AI network will take over the action, the user may deliberately jump left many times to cause the AI network to have sufficient confidence to take control of this gesture.

When one or more gestures are to be controlled by the AI network, there should be no further learning, i.e., no further refinement of the weights in the AI network for the gestures that have entered the controlling phase. In some instances, the user may no longer need to provide the training data, i.e., in the game example, the user no longer needs to move a finger to create the gesture to shoot.

Experiments in the field have indicated that the EEG of the user does not change if the user ultimately does not take an action. Rather, it is the user's intent which results in the EEG signal, not the action itself. Thus, in an ideal implementation, a user will be able to cause the AI network to initiate commands without the user actually taking any action.

However, from the perspective of the AI network, normally the absence of the user's finger action, and thus the shoot gesture originating in the controller, would be a counter productive event, as the learning algorithm would now associate the detected EEG signal with no action and begin to adjust the weights such that the weights of the shoot gesture would reduce. There would be no labeled data to refine the gesture, and the weights for the gesture would appear to be a false classification to be deprecated as the learning proceeds.

This situation may be avoided in various ways. In some embodiments, the weights contributing to the gesture that has entered the controlling phase are locked, and are thus no longer able to update, and any commands from the controller may be ignored, whether or not the user is still performing gestures on the controller. Alternatively, when it initiates the command to the computing system corresponding to the action, the AI network may create "false" training data, i.e., the AI network may treat its own command as a training data item, or labeled input, to be fed to the unmodified learning algorithm.

Using the training procedure described above, system 100 will eventually be able to predict many, if not all, of the gestures of the user, and thus be able to enter the controller phase. At this point, the user's experience will be that the machine, game, robot, or whatever computer system is being controlled, is largely or entirely responding to the EEG signals alone and will not require an action by the user to be activated (at least for those gestures in the controlling phase).

As above, the EEG signal correlated to a gesture will have occurred some number of milliseconds before the actual gesture occurs. This delay between detection of the EEG signal and the user's gesture has been taken into account in the learning phase as the AI network correlates EEG signals to the user's gestures, as the AI network using the LSTM or RNN (or other means) will have learned that the EEG signal arriving some many milliseconds ago is that which optimally correlates to the labeled data, to the gesture that ultimately occurs.

In this situation, an issue arises of when the AI network should initiate the command corresponding to the detected EEG signal. In one embodiment, the AI network may be constructed to initiate the command corresponding to the detected EEG signals at a time approximately equal to the time the command would be received by the computing system from the controller, i.e., when an average user would take the action, for example, 200 milliseconds after the detection of the EEG signal.

In other embodiments, the AI network need not initiate the command at the same time a controller command would be received. Rather, a means may be provided to reduce the time delay between the detection of the EEG signal and the command initiated by the AI network.

If such a means is present, the AI network, which has previously provided a global delay of commands compared to detection of the EEG signals, may instead reduce the delay between detection of an EEG signal and initiation of the corresponding command. In such a case, the user will see the result of the commands from the AI network begin to come faster than the commands which came from the user in the learning phase.

A sudden reduction of delay in issuing commands by the AI network may be unnerving or confusing to a user, particularly if there has been no indication of how close the AI network is to being able to take over the issuance of commands, such as the visual bar graph described above. Thus, in some embodiments, the delay may be introduced gradually to allow the user to become accustomed to the "new" control environment of reduced delay before the maximum reduction of delay is implemented. For example, the delay may be reduced by a certain number of milliseconds at intervals, or may be reduced on some type of exponential curve, etc.

Reducing the delay between detection of an EEG signal and the corresponding command may allow the user to experience a boost in performance of the game or other computing system, as events controlled by the AI network are now occurring faster than when controlled by the user.

However, in some cases reducing the delay between detection of an EEG signal and the initiating of a corresponding command may be counterproductive, as in some instances the reduction of the delay between detection of the EEG signal and the time when the user would have taken action may actually lead to deteriorating performance of the task, the game or the robot control. At that point the user may wish to begin to provide control again.

For this reason, a means may be provided by which the user may indicate that the delay has been reduced too much and that the user wished to take over from the AI network; in such a case the delay may be returned to a point prior to that where the user intervened. In some embodiments, for example, the AI network may observe that a user who has previously stopped using the controller has again started using it, thus indicating that the user wishes to once more assert manual control, rather than allowing the AI network to act. In other cases, the AI network may be constructed to pause its commands periodically and see if the user resumes gestures on the controller to insure that performance remains acceptable to the user.

In various embodiments, the AI network may either increase the delay gradually, and await further cues from the user as to whether performance of the computing system has improved sufficiently, may continue to issue commands to the computing system with no reduction of delay, or may return complete control to the user to enter commands on the controller.

Figure 2:
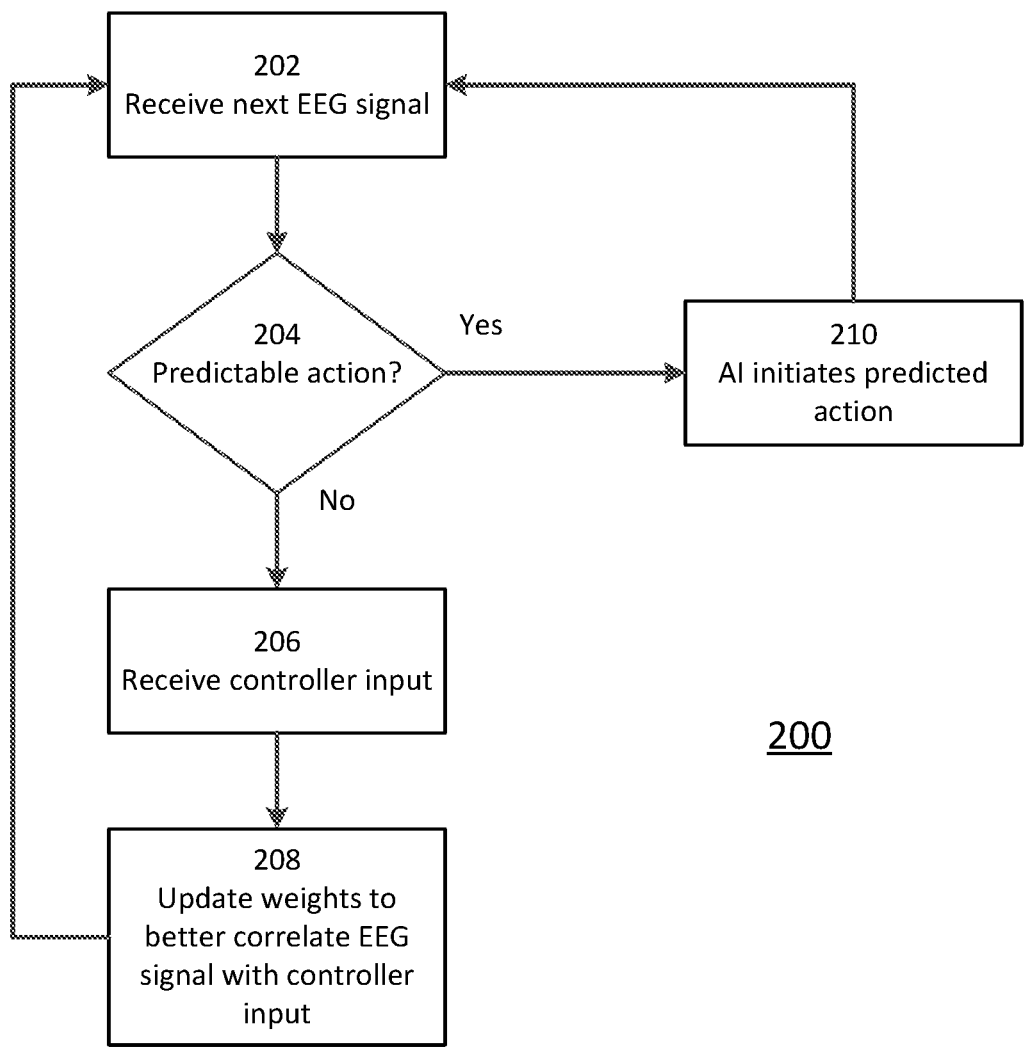
FIG. 2 is a flow chart of a method for controlling the actions of a computing system based upon the EEG of a user according to one embodiment.

FIG. 2 is a flow chart of a method 200 for controlling the actions of a computing system based upon the EEG of a user according to one embodiment.

At step 202, an AI network, such as AI network 108 of FIG. 1, receives an EEG signal from an EEG detector such as EEG detector 106 of FIG. 1. At step 204, the AI network determines whether it is able to predict a user action from the received EEG signal.

When the AI network determines at step 204 that it is not able to predict a user action from the received EEG signal, the AI network remains in the learning phase as discussed above. Thus, at step 206 the AI network receives the next input controller command, for example, from controller 104 of FIG. 1, which corresponds to some user action on the controller and is presumed to correspond to the most recently received EEG signal. The controller command also goes to the computing system, such as computing system 102 in FIG. 1, and causes the computing system to take some action.

At step 208 the AI network updates weights in one or more of its layers to better correlate the received EEG signal with the received controller input. The process then returns to step 202 to await the next EEG signal.

At step 204, when the AI network determines that it is able to predict a user action from the received EEG signal, at step 210 the AI network initiates the predicted action by issuing a command to the computing system that commands the computing system to take the action, as if the computing system had received the command from the controller. The process then again returns to step 202 to await the next EEG signal.

Figure 3:
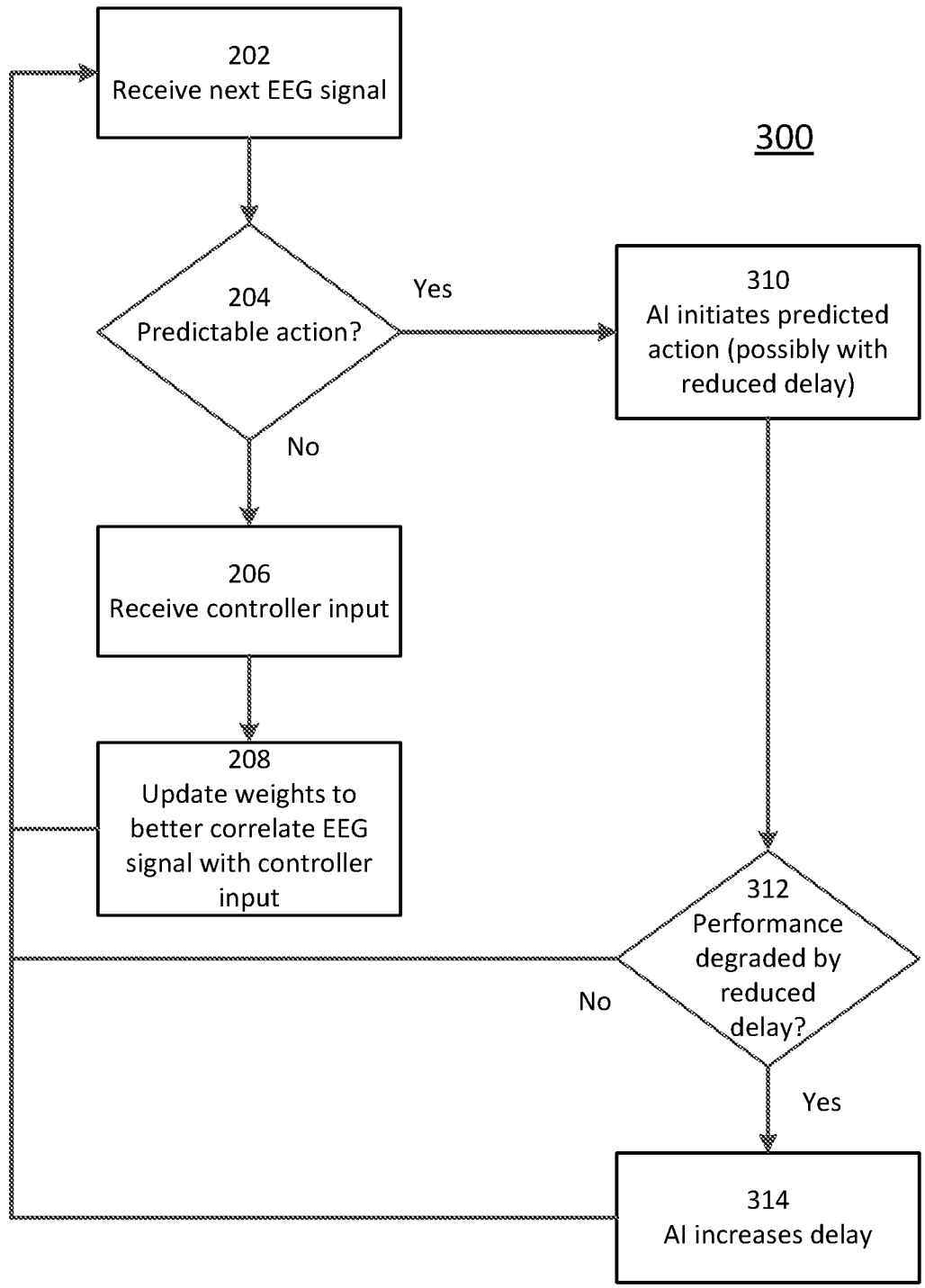
FIG. 3 is a flow chart of a method for controlling the actions of a computing system based upon the EEG of a user according to another embodiment.

FIG. 3 is a flow chart of a method 300 for controlling the actions of a computing system based upon the EEG of a user according to another embodiment. In method 300, steps 202 to 208 are the same as steps 202 to 208 in method 200 of FIG. 2.

In method 300, when the AI network, again such as AI network 108 of FIG. 1, determines that it is able to predict a user action from the received EEG signal at step 204, the method now goes to step 310. While the AI network initiates the predicted action at step 310, as it does at step 210 of method 200 above, now the action may be initiated with a reduced delay from detection of the EEG signal as described above.

In method 300, rather than immediately returning to step 202 after step 310, at step 312 the AI network determines whether there is an indication of degraded performance of the computing system, again such as computing system 102 of FIG. 1, as a result of the reduced delay. As above, this may be determined based upon some action of the user indicating that the performance is no longer regarded as improved or satisfactory.

If there is no indication of degraded performance, the method returns to step 202 to await the next EEG signal. If, on the other hand, there is degraded performance, the AI network increases the delay as described above until the performance of the computing system is satisfactory. The method then again returns to step 202 to await the next EEG signal.

The disclosed system has been explained above with reference to several embodiments. Other embodiments will be apparent to those skilled in the art in light of this disclosure. Certain aspects of the described method and apparatus may readily be implemented using configurations other than those described in the embodiments above, or in conjunction with elements other than or in addition to those described above.

For example, as is well understood by those of skill in the art, various choices will be apparent to those of skill in the art. As above, the AI network may be contained within the computing system. Further, the illustration of a single AI network is exemplary; one of skill in the art will be able to select an appropriate number AI networks that is appropriate for a particular application.

These and other variations upon the embodiments are intended to be covered by the present disclosure, which is limited only by the appended claims.

What is claimed is:

1. A method of controlling a computing system that performs actions based upon input from a controller that represents actions of a user, comprising:
   receiving by an electroencephalograph (EEG) detector an EEG signal representing the brain wave activity of a user;
   determining by an artificial intelligence (AI) network a likelihood that an action of the user can be predicted based upon the EEG signal;
   when the likelihood that the action of the user can be predicted exceeds a predetermined threshold, initiating by the AI network an AI network input to the computing system that represents the predicted action of the user;
   receiving at the computing system and the AI network an input from the controller representing the action of the user; and
   updating by the AI network weights in the AI network to better correlate the received EEG signal with the input received from the controller;
   wherein initiating by the AI network the AI network input to the computing system further comprises substituting by the AI network the AI network input for the controller input;
   wherein initiating by the AI network the AI network input to the computing system further comprises initiating the AI network input to the computing system before the controller input would be received by the computing system;
   wherein initiating by the AI network the AI input to the computing system further comprises:
      determining that initiating the AI network input to the computing system before the controller input has degraded the performance of the computing system; and
      wherein initiating by the AI network the AI network input to the computing system is delayed while still being before the controller input would be received by the computing system.

2. A system for controlling a computing system that performs actions based upon input from a controller that represents actions of a user, comprising:
   an electroencephalograph (EEG) detector configured to receive an EEG signal representing the brain wave activity of a user; and
   an artificial intelligence (AI) network configured to:
      determine a likelihood that an action of the user can be predicted based upon the EEG signal;
      when the likelihood that the action of the user can be predicted exceeds a predetermined threshold, initiate an AI network input to the computing system that represents the predicted action of the user; and
      update weights in the AI network to better correlate the received EEG signal with the input received from the controller;
   wherein the AI network is further configured to initiate the AI network input to the computing system by substituting the AI network input for the controller input;
   wherein the AI network is further configured to initiate the AI network input to the computing system before the controller input would be received by the computing system;
   wherein the AI network is further configured to:
      determine that initiating the AI network input to the computing system before the controller input has degraded the performance of the computing system; and
      delay initiating the AI network input to the computing system while still initiating the AI network input before the controller input would be received by the computing system.

3. The system of claim 2 wherein the AI network is a recurrent neural network.

4. The system of claim 3 wherein the AI network is a long short-term memory neural network.

5. The system of claim 3 wherein the AI network is a Jordan neural network.

6. The system of claim 3 wherein the AI network is an Elman neural network.

* * * * *